United States Patent [19]

Kirchner

[11] Patent Number: 4,516,576
[45] Date of Patent: May 14, 1985

[54] TOURNIQUET STRAP OR BAND FOR RESTRICTING BLOOD FLOW, ESPECIALLY FOR TAKING BLOOD SAMPLES

[75] Inventor: Georg Kirchner, Markröningen, Fed. Rep. of Germany

[73] Assignee: Sanimed Vertrieb AG, St. Gallen, Switzerland

[21] Appl. No.: 479,445

[22] Filed: Mar. 28, 1983

[30] Foreign Application Priority Data

Apr. 1, 1983 [CH] Switzerland ............... 2011/82

[51] Int. Cl.³ .............................................. A61B 17/12
[52] U.S. Cl. .................................. 128/327; 128/686; 24/171
[58] Field of Search ............... 128/326, 327, 686; 24/171

[56] References Cited

U.S. PATENT DOCUMENTS

| 303,187 | 8/1884 | Riesenberg | 24/171 |
|---|---|---|---|
| 691,690 | 1/1902 | Wroe | 24/171 |
| 1,299,860 | 4/1919 | Plummer | 128/327 |
| 1,332,442 | 3/1920 | Kane . | |
| 2,113,534 | 4/1938 | Brown | 128/327 |
| 2,756,753 | 7/1956 | Means | 128/327 |
| 3,958,575 | 5/1976 | Von Soiron | 128/327 |
| 4,211,289 | 7/1980 | Klein | 128/327 |

FOREIGN PATENT DOCUMENTS

| 746649 | 5/1943 | Fed. Rep. of Germany | 128/327 |
|---|---|---|---|
| 1275815 | 8/1968 | Fed. Rep. of Germany . | |
| 2824037 | 12/1979 | Fed. Rep. of Germany . | |
| 1087010 | 10/1967 | United Kingdom | 24/171 |

Primary Examiner—C. Fred Rosenbaum
Assistant Examiner—Gene B. Kartchner
Attorney, Agent, or Firm—Werner W. Kleeman

[57] ABSTRACT

Tourniquet for medical applications, for example, for stanching the blood in veins for taking blood samples, wherein the tourniquet comprises a clamping lock and a strap which is pulled through the clamping lock and wrapped around the arm of a patient. Clamping of the strap in order to form a stanching loop occurs by means of a spring-loaded clamping wedge which clamps the strap against an inner wall of the clamping lock via a clamping plate. By manually displacing the clamping wedge against the force of the spring, the clamping force can be sensitively regulated, so that a regulated release of the stanching loop is possible. In all these manipulations the tourniquet can be single-handedly operated.

6 Claims, 1 Drawing Figure

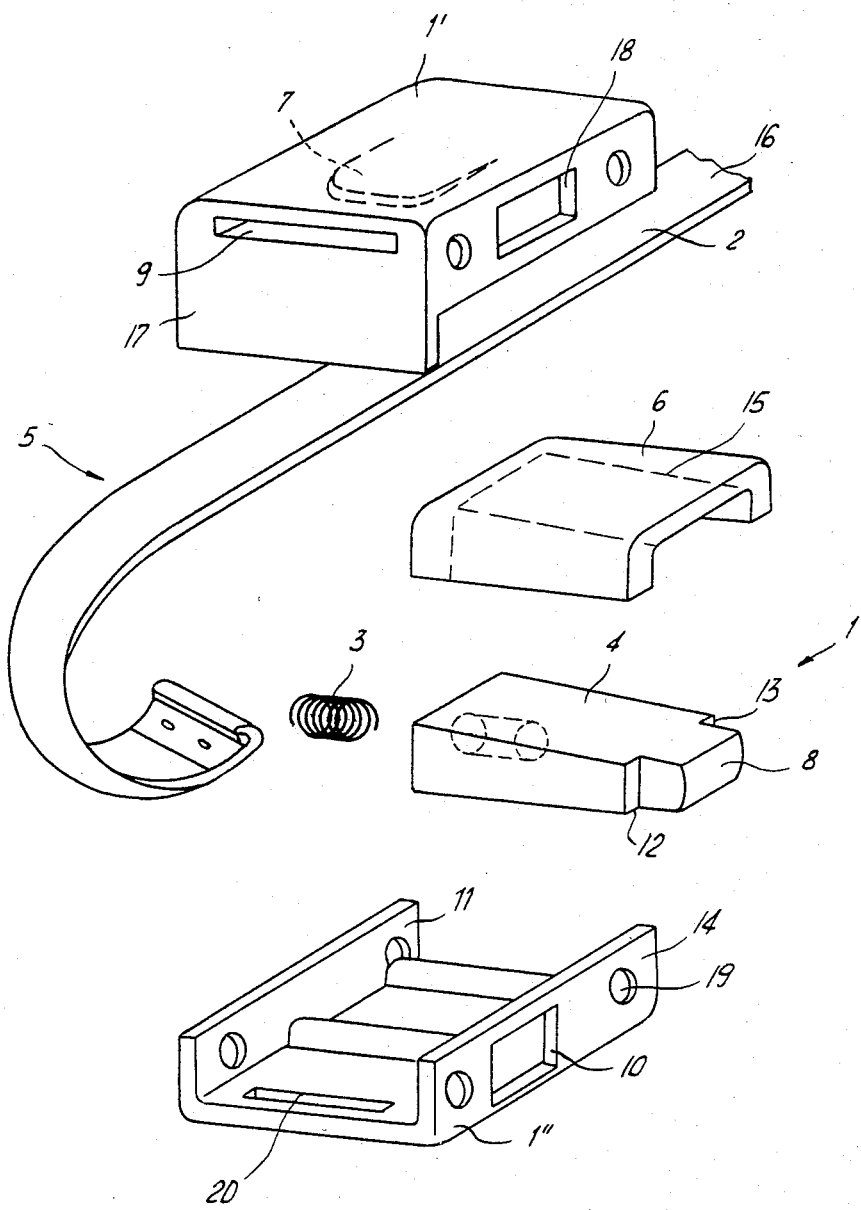

TOURNIQUET STRAP OR BAND FOR RESTRICTING BLOOD FLOW, ESPECIALLY FOR TAKING BLOOD SAMPLES

BACKGROUND OF THE INVENTION

The present invention relates to a new and improved tourniquet.

The present invention also relates to a new and improved clamping lock for use with a tourniquet.

The invention relates specifically to a new improved tourniquet containing a clamping lock and a strap which can be pulled through the clamping lock and can be suspended in the same at one of its ends in order to form a stanching loop.

Tourniquets of the aforementioned type for medical applications like, for example, for stanching the arm of a patient, in known designs comprise a slit in the clamping lock for the self-locking passage of an elastic band, one end of which can be suspended at a spring-loaded flap linked to the clamping lock in order to form the stanching loop.

To tighten the stanching loop, for example, around the arm of a patient, tension is applied to the free end of the strap which projects from the clamping lock. To release the stanching loop the flap is actuated against the force of the spring, whereby the suspended end of the strap is released.

It is disadvantageous in such a tourniquet that the disengagement of the strap occurs immediately after actuation of the flap. As a consequence thereof the strap tension cannot be decreased in a regulated way during the medical work. Such a regulated reduction in the strap tension and thus the level of the blood stanching in the blood vessels is frequently required. Additionally, if the tourniquet has to be completely released and tightened anew, then such frequently impedes or prolongs the medical work in an impermissible manner. In particular a single-handed operation for manipulating the tourniquet is impossible during a prolonged stanching process when using the aforementioned design.

SUMMARY OF THE INVENTION

Therefore, with the foregoing in mind it is a primary object of the present invention to provide a tourniquet which can be single-handedly operated, i.e. that after formation of the stanching loop the tightening thereof as well as the regulated or complete release thereof can be single-handedly performed.

Now in order to implement this and still further objects of the invention, which will become more readily apparent as the description proceeds, the tourniquet of the present development is manifested by the features that the clamping lock contains a clamping wedge which is displaceable against the force of a spring and in its operative position, due to the spring, clampingly presses the strap against a wall of the clamping lock in order to prevent opening of the stanching loop, wherein the clamping of the strap is releasable by adjustment of the clamping wedge against the force of the spring.

As alluded to above, the invention is not only concerned with the aforementioned tourniquet, but also relates to a novel construction of a clamping lock for use with the tourniquet. Generally speaking, the inventive clamping lock contains a strap which can be pulled therethrough and can be suspended therein at one of its ends to form a stanching loop.

To achieve the aforementioned measures the inventive clamping lock for use with a tourniquet, wherein a strap can be pulled through the clamping lock and can be suspended in the clamping lock at one of its ends to form a stanching loop, in its more specific aspects, comprises a clamping wedge which is displaceable against the force of a spring and in its operative position is held against a wall of the clamping lock due to the spring.

In preferred designs of the tourniquet or of the clamping lock according to the invention the clamping wedge can be positioned transverse to the longitudinal axis of the strap or, respectively, parallel to the longitudinal axis of the strap.

Advantageously a clamping plate can be arranged in the clamping lock between the clamping wedge and the strap or, respectively, the wall of the clamping lock.

The clamping lock may also contain a wedge surface at the region of the clamping wedge at the inner side facing the wedge.

BRIEF DESCRIPTION OF THE DRAWING

The invention will be better understood and objects other than those set forth above, will become apparent when consideration is given to the following detailed description thereof. Such description makes reference to the annexed drawing wherein the single FIGURE shows an exploded view of the essential elements of a tourniquet according to the invention prior to their assembly.

DETAILED DESCRIPTION OF THE PREFERRED EMBODIMENTS

Describing now the drawing, it is to be understood that only enough of the construction of the tourniquet or clamping lock for use with the tourniquet has been shown as needed for those skilled in the art to readily understand the underlying principles and concepts of the present development, while simplifying the showing of the drawing. Turning now to the single FIGURE of the drawing, there has been illustrated therein a tourniquet which comprises a clamping lock 1 containing an upper member 1' and a lower member 1" and a strap 2 which is pulled through the clamping lock 1 and which is force- and/or form-lockingly held therein and which is releasably suspended at one of its ends in a slit of the lower member 1" for the formation of a stanching loop 5. Into the lower member 1" a clamping wedge 4 is transversely displaceably placed transverse to the longitudinal axis of the clamping lock 1 which clamping wedge 4 projects from the lower member 1" by means of a grip extension 8 defining an actuating element. Opposite to the grip extension 8 a spring 3 engages the clamping wedge 4 and is supported at the lower member 1". A clamping plate 6 rests so as to be vertically displaceable on the clamping wedge 4 in order to areally clamp the strap 2 passing through between the clamping plate 6 and the upper member 1'. The upper member 1' possesses an entrance slit 9 for the strap 2 at one of its end walls 17 and a recess for the grip extension 8 of the clamping wedge 4 at one of its narrow longitudinal sides.

The members of the clamping lock 1 as illustrated in the drawing can be assembled on the basis of the foregoing description as follows:

The clamping wedge 4 is inserted into the lower member 1" by sticking the grip extension 8 thereof through a window 10 in the lower member 1" as seen from the inside of the lower member 1". Simultaneously, the spring 3 is placed between that side of the clamping wedge 4 which is remote from the grip extension 8 and the side wall 11 of the lower member 1″, whereby the clamping wedge 4 is pressed against the other side wall 14 of the lower member 1″ by the shoulders 12 and 13 on both sides of the grip extension 8. The clamping plate 6 thereafter is placed upon the clamping wedge 4 such that the clamping wedge 4 is positioned in the recess 15 of the clamping plate 6. Thereafter, the strap 2 is pulled with its free end 16 through the entrance slit 9 of the upper member 1′ and again pulled out therefrom at the opposite side. The upper member 1′ including the strap 2 pulled therethrough is then seated on the clamping plate 6 such that the grip extension 8 also projects through a window 18 of the upper member 1′. The openings 19 serve for insertion of mounting members, so that the upper member 1′ and the lower member 1″ can be interconnected.

When using the tourniquet the strap 2 is laid, for example, around the upper arm of the patient and is suspended at its free end in a slit 20 in the lower member 1″. Tension is then applied to the free end of the strap 2 until the stanching loop is closely tightened and a stanching action occurs in the arm of the patient. If the stanching effect is too large, particularly during prolonged stanching, then the clamping wedge 4 can be somewhat displaced by inwardly pushing the grip extension 8 in a regulated manner. The friction generated at both sides of the strap 2 by the force acting normally thereto is thus decreased and the strap 2 can slide somewhat in the direction of the stanching loop. To fully release the stanching loop the grip extension 8 is fully pushed inwardly, the tensioning force on the strap 2 is released, and thus, the disengagement of the end of the strap 2 on the side of the loop is effected.

In a different embodiment (not shown) the clamping wedge is arranged for displacement in the axial direction of the strap 2. Above all, this embodiment offers the advantage that a longer clamping wedge can be used, and thus, the stanching loop can be released with a more sensitive regulation.

In a further embodiment the upper member 1′ possesses a wedge surface 7 indicated by broken lines at a location opposite the clamping plate 6, which clamping surface deforms appropriately selected materials of the strap due to the constriction which results in this way and thereby partially and positively holds the strap. Instead of the wedge surface 7 ribs, serving as slippage retarders, can be provided in any direction which extends diagonally or just approximately diagonally.

While there are shown and described present preferred embodiments of the invention, it is to be distinctly understood that the invention is not limited thereto, but may be otherwise variously embodied and practiced within the scope of the following claims. Accordingly,

What I claim is:

1. A tourniquet comprising:
 a clamping lock having a wall;
 a strap capable of being pulled through said clamping lock and of being suspended in the same at one of its ends to form a stanching loop;
 said strap defining a longitudinal axis and a plane;
 an adjustable clamping wedge contained in said clamping lock and being displaceable substantially transversely to said longitudinal axis of said strap and substantially parallel to said plane of said strap against the force of a spring;
 a spring acting upon said adjustable clamping wedge;
 said clamping wedge, in an operative position thereof and due to the action of said spring, clampingly pressing said strap with a clamping force against said wall of said clamping lock in order to prevent unintentional opening of said stanching loop;
 an actuating element protruding from the clamping lock in order to displace said clamping wedge for releasing said strap from the action of said clamping force; and
 said actuating element constituting a grip extension of said clamping wedge.

2. The tourniquet as defined in claim 1, further including:
 a clamping plate arranged in said clamping lock between said clamping wedge and said strap.

3. The tourniquet as defined in claim 1, wherein:
 said clamping lock possesses at an inner side of said wall a wedge surface at the region of said clamping wedge and which wedge surface bears against said strap.

4. A clamping lock for use with a tourniquet containing a strap having a longitudinal axis and which can be pulled through the clamping lock in the direction of said longitudinal axis of the strap and can be suspended in the clamping lock at one of its ends to form a stanching loop, said clamping lock having a longitudinal axis and comprising:
 a wall;
 a clamping wedge positioned transverse to said longitudinal axis of the clamping lock and transverse to said longitudinal axis of the strap which can be pulled through the clamping lock;
 a spring acting upon said clamping wedge;
 said clamping wedge being displaceable against the force of said spring and transversely with respect to the longitudinal axis of the strap and in its operative position being biased towards said wall of the clamping lock due to the action of said spring; and
 an actuating element constituting a grip extension of said clamping wedge for releasing the biasing of said clamping wedge towards said wall of said clamping lock.

5. A clamping lock for use with a tourniquet containing a strap which can be pulled through the clamping lock and can be suspended in the clamping lock at one of its ends to form a stanching loop, said clamping lock having a longitudinal axis and comprising:
 a wall;
 a clamping wedge positioned transverse to said longitudinal axis of the clamping lock;
 a spring acting upon said clamping wedge;
 said clamping wedge being displaceable against the force of said spring and in its operative position being biased towards said wall of the clamping lock due to the action of said spring;
 an actuating element constituting a grip extension of said clamping wedge for releasing the biasing of said clamping wedge towards said wall of said clamping lock and
 a clamping plate seated upon said clamping wedge and pressed thereby against said wall of said clamping lock.

6. The clamping lock as defined in claim 4, wherein:
 said wall of said clamping lock is situated opposite said clamping wedge and possesses a wedge surface.

* * * * *